United States Patent [19]

Winnick

[11] 4,045,419

[45] Aug. 30, 1977

[54] CHEMICAL PROCESS FOR PRODUCING ISOPRENE BY PYROLYSIS OF ALLYLIC ESTERS

[75] Inventor: Charles N. Winnick, Teaneck, N.J.

[73] Assignee: Halcon International, Inc., New York, N.Y.

[21] Appl. No.: 528,103

[22] Filed: Nov. 29, 1974

Related U.S. Application Data

[60] Continuation of Ser. No. 318,942, Dec. 27, 1972, abandoned, which is a division of Ser. No. 638,659, May 15, 1967, abandoned, which is a continuation-in-part of Ser. No. 543,802, April 20, 1966, abandoned.

[51] Int. Cl.$^2$ .......................... C07C 1/00; C07C 1/20; C07C 5/42
[52] U.S. Cl. ........................... 260/681; 260/497 A
[58] Field of Search ........................... 260/681, 497 A

[56] References Cited

U.S. PATENT DOCUMENTS

| 1,050,354 | 1/1913 | Earle | 260/681 |
|---|---|---|---|
| 1,098,859 | 6/1914 | Webel | 260/681 X |
| 2,345,113 | 3/1944 | Guggemor et al. | 260/681 |
| 2,398,103 | 4/1946 | Long | 260/681 X |
| 2,428,590 | 10/1947 | Shohol et al. | 260/497 A |
| 3,391,215 | 7/1968 | Winnick | 260/681 |

*Primary Examiner*—Winston A. Douglas
*Assistant Examiner*—John F. Niebling
*Attorney, Agent, or Firm*—William C. Long; David Dick; Riggs T. Stewart

[57] ABSTRACT

Process for preparing unsaturated esters by reacting an olefin having an allylic hydrogen atom with an ester forming material in the presence of oxygen and a catalyst selected from the group consisting of mercury, selenium or tellurium. The unsaturated ester may be converted to a polyunsaturated compound by pyrolysis.

6 Claims, No Drawings

CHEMICAL PROCESS FOR PRODUCING ISOPRENE BY PYROLYSIS OF ALLYLIC ESTERS

RELATED APPLICATION

The present application is a continuation of Ser. No. 318,942, filed Dec. 27. 1972 now abandoned; which is a division of Ser. No. 638,659, filed May 15, 1967 now abandoned, and which is a continuation-in-part of co-pending patent application Ser. No. 543,802 filed Apr. 20. 1966 now abandoned.

BACKGROUND OF THE INVENTION

The invention relates to the preparation of unsaturated esters and to the conversion of these esters to polyunsaturated compounds. Prior art methods for preparing unsaturated esters by reacting an olefin and an acid were adversely affected by small amounts of water and required expensive catalysts. Accordingly, it is an object of the present invention to provide a new and improved process for preparing unsaturated esters. Another object is to provide new catalysts for this reaction. Still another object is to provide a new and improved method for preparing polyunsaturated compounds.

SUMMARY OF THE INVENTION

The present invention provides a process for preparing unsaturated esters which are precursors of polyunsaturated compounds wherein an olefinically unsaturated compound having allylic hydrogen atom is reacted with an ester forming material, such as a carboxylic acid or an acid anhydride in the presence of an oxidizing agent containing molecular oxygen and a catalyst selected from the group consisting of mercury, selenium or tellurium, or an oxide, salt, or complex of said metals, or mixtures of any two or more of the foregoing, the reaction being carried out at pressures of from about 0.5 atmosphere to about 70 atmospheres and at temperatures of from about 60° C to about 200° C.

DETAILED DESCRIPTION

According to one embodiment of the present invention an olefinically unsaturated compound having an allylic hydrogen, that is, a labile hydrogen atom on a carbon atom alpha to a double bond, is reacted with a material which forms an ester therewith, such as, e.g., a carboxylic acid, or an acid anhydride. The reaction which is carried out in the presence of oxygen and a catalyst may be described as an oxidative acylation, or acyloxylation. Organic acids are suitable ester forming materials. The simplest such material suitable for use in the present invention is acetic acid.

Any olefin containing a labile hydrogen atom on a carbon atom adjacent to a double bond may be used in the process of the present invention. The simplest such olefin must contain three carbon atoms. The olefinically unsaturated compound may be an aliphatic, cycloaliphatic, or alkylaryl straight-chain or branched chain compound containing one or more double bonds. The olefinically unsaturated compound may be a hydrocarbon or a compound containing hetero-atoms in the molecule, for example, 3 butenoic acid. Examples of suitable olefins are propylene, butene-1,butene-2, any of the methylbutene isomers, n-pentene-1, n-hexene-1, n-octene-1,cyclohexene, 3,5,5-trimethylhexene-1 or alpha ethyl styrene.

As the ester forming material there may be used aliphatic, monocarboxylic acids, preferably, monocarboxylic, saturated acids having from 2 to 20 carbon atoms and especially those having from 2 to 8 carbon atoms in a straight or branched chain. Examples of such acids are, for example, acetic, propionic, butyric, isobutyric, n-hexancic, lauric, myristic, palmitic and stearic.

The reaction may be conducted in vapor or liquid phase at temperatures from about 30° C. to about 200° C., preferably from about 100° C. to about 180° C., and most preferably from about 115° C. to about 150° C., and at pressures from about 0.5 atmosphere to about 70 atmospheres, preferably from about 0.9 atmosphere to about 10 atmospheres, and most preferably from about 1 atmosphere to about 5 atmospheres. In liquid phase olefin concentration may be from about 1% to about 5%, preferably from about 5% to about 25%. When operating in vapor phase, the feed will contain the following ranges of the specified materials:

|  | Broad | Preferred | Most Preferred |
| --- | --- | --- | --- |
| Mol % olefin | 3–37 | 20–95 | 70–90 |
| Mol % acid | 1–95 | 2–40 | 5–10 |
| Mol % $O_2$ | 2–96 | 4–20 | 5–10 |

The esterification reaction is catalyzed by Se, Te or Hg, or compounds or complexes of these metals, such as their oxides and inorganic and organic salts. Specific examples of such compounds are HgO, mercuric acetate, mercuric nitrate, mercury acetyl acetonate, $HgSO_4$, $SeO_2$, $TeO_2$. When operating in liquid phase, the amound of catalyst (expressed as free metal) may vary from about 0.001% by weight to about 10% by weight of the reaction mixture, preferably from about 0.1% to about 5%. While amounts of catalyst greater than 10% may be employed, there is generally no advantage to be obtained from such high levels. When operating in vapor phase, the catalyst may conveniently be deposited on a support having a surface area greater than 1 m²/g. Suitable supports are, for example, activated carbon, alumina, silica, spinels, titania, silica aluminas, zirconia molecular sieves, etc.

From about 0.1% to about 20% of the combined weight of the catalyst and support consists of Hg, Se, or Te, in the form of a salt, oxide, complex or metal itself. Preferably the catalyst accounts for about 1-15% by weight and most preferably from about 4-10% by weight. In addition, the catalyst may contain one or more promoters selected from the group consisting of Cu, Fe, Ni, Co, Cr or Mn in the form of a salt, an oxide, a complex or free metal. Particularly preferred as promoters are compounds of Fe and Cu. Alkaline earth metal oxides or salts may also be present.

It is preferable to employ a ridox system as co-catalyst together with the catalyst. Redox systems are well known and their use will be readily understood by those skilled in the art. As examples of suitable redox systems there may be mentioned redox salts of copper, for example cupric acetate, or ferric salts, for example ferric acetate. Metal salts corresponding to the ester which it is desired to produce are also particularly suitable. It is also possible to employ organic and inorganic redox systems in conjunction. Iron or copper, alone or in combination may be employed as a co-catalyst. The preferred co-catalyst is a mixture of iron and copper salts, preferably the organic acid salts of these metals. The co-catalyst or catalysts are employed at mol ratios of from about 0.01 to about 100 with respect to the catalyst. The ratio of iron to copper may vary from about 10:1 to about 1:10, preferably from about 6.9:1 to about 1:6.9, and most preferably the amount of copper exceeds that of iron.

Any molecular oxygen containing material, for example air, oxygen, oxygen enriched air, oxygen depleted air, or mixtures of oxygen and inert gas may be used as the source of oxygen. Theoretically, one half mol of oxygen is required per mol of the unsaturated compound.

Salts of alkali and alkaline earth metals corresponding to the acid employed may be used but are generally not necessary. Anhydrides may be present but also are not necessary.

The reaction may be considered to involve an oxidative acylation, or acyloxylation of the olefin in the presence of the catalyst. For example, in the case of 2-methyl butene-1 and acetic acid, the reaction may proceed as follows:

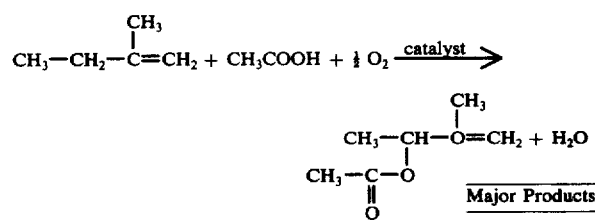

The foregoing reaction is not significantly affected by the presence of water which in the presence of other catalysts, e.g., Pd, is known to result in the formation of significant amounts of aldehydes or ketones. The use of the catalysts of the present invention permits obtaining higher selectivities of the desired allylic acetates and eliminates the necessity of starting with anhydrous materials. Water may be present in the initial reaction mixture in an amount up to about 40% by weight, although water levels of about 15% or less are preferred.

The unsaturated ester may be converted to a poly unsaturated compound by being subjected to pyrolysis at temperatures of from about 250° C. to about 550° C., preferably, from about 350° C. to about 450° C. Atmospheric pressure is preferred although pressures of from 0.1 to 10 atmospheres may be employed. Such treatment converts the unsaturated ester into the poly unsaturated compound and an acid. For example, butenyl acetate cracks to yield butadiene and acetic acid.

The ester product obtained according to the reaction of the present invention is actually a mixture of isomeric allylic esters, although some saturated ester may be formed in minor amounts from addition of acid across the olefinic double bond. In some cases, addition of water to the unsaturated ester yields a glycol monoester as a by-product. These by-products are useful since the acid adduct, the saturated ester, cracks reforming the original olefin and the glycol acetate monoester cracks to the diolefin. For example, in the case of butene-1 the major products are:

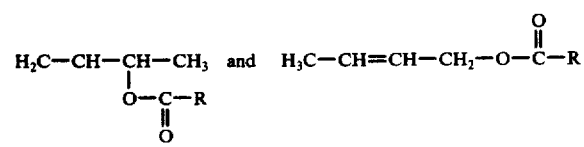

In the case of methyl butene the products may include:

| Major Products | By Products |
|---|---|
| (a) H₃C—CH—C(CH₃)—CH₂—O—C(O)—R | (d) H₃C—CH₂—C(CH₃)(OH)—CH₂—O—C(O)—R |
| (b) H₃C—O=CH—CH₂—O—C(O)—R, CH₃ | (e) H₃C—CH(OH)—C(CH₃)—CH₃, O—C(O)—R |
| (c) H₂O=CH—CH₂—CH₃, CH₃, O—C(O)—R | (f) H₃C—CH₂—C(CH₃)(O—C(O)—R)—CH₃ |

2-methyl butene-1 isomerizes during the reaction to about a 50/50 mixture of 2-methyl butene-1 and 2-methyl butene-2. No isomerization is observed when the latter compound is used as starting material. Compounds (a) and (b) being esters of primary alcohols, will have boiling points, in the case of the acetate ester of about 150° C. while compound (c) will have a lower boiling point, about 130° C. in the case of the acetate ester. All of the foregoing materials, except compound (f) may be readily converted to the correspnding diolefin, e.g., butadiene is obtained if the starting material is butene, and isoprene is obtained if the starting material is methyl butene. The pyrolysis proceeds according to the following equation:

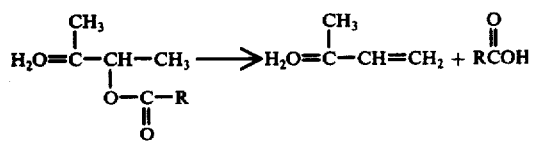

A particular advantage of the present invention is that the intermediate esters may be readily separated from unreacted olefins before cracking the ester thus providing a polyolefinic compound uncontaminated with mono-olefin (or paraffins) and eliminating costly purification procedures. In the methyl butene-acetic acid system, any t-amyl acetate formed, cracks during acetic acid distillation to yield the starting olefin and acetic acid so that the allylic acetates and any glycol acetate, which yield diolefin on cracking, are easily obtained free from the simple adduct, t-amyl acetate.

The following examples illustrate the present invention without however, limiting the same thereto. In the examples illustrating the formation of unsaturated esters, the reaction vessel is a 300 cc, autoclave with oxygen being pressured in.

EXAMPLE 1

130 grams of glacial acetic acid are reacted with 40 grams of 2-methyl-1-butene at 120° C. for 2 3/4 hours under oxygen pressure of about 95 psig in the presence of a catalyst consisting of 8 grams of mercuric acetate and a co-catalyst consisting of 5.0 grams of basic ferric acetate and 0.75 grams of cupric acetate. 0.25 moles of oxygen are absorbed during the course of the reaction. The reaction product contains 0.0999 moles of unsaturated esters, and 0.015 moles each of C-5 glycol monoacetate and t-amyl acetate. Olefin conversion is 0.34 moles. The selectivity, defined as moles of isoprene precursors (i.e., unsaturated esters, and glycol monoand di-esters) divided by moles of reacted olefin less moles of t-amyl acetate formed, is 35%.

EXAMPLE 2

130 grams of glacial acetic acid are reacted with 40 grams of 2-methyl-1-butene at 120° C. for 1 2/3 hours under oxygen pressure of about 125 psig in the presence of 10 grams of sodium acetate and a catalyst consisting of 8 grams of mercuric acetate and a co-catalyst consisting of 1 gram of basic ferric acetate and 0.15 grams of cupric acetate. 0.25 moles of oxygen are absorbed during the course of the reaction. The reaction product contains 0.077 moles of unsaturated esters and 0.014 moles of t-amyl acetate. Olefin conversion is 0.36 moles and selectivity (defined as in example 1) is 22%.

EXAMPLE 3

130 grams of glacial acetic acid are reacted with 40 grams of 2-methyl-2-butene at 120° C. for 3 hours under oxygen pressure of about 260 psig in the presence of 10 grams of sodium acetate and a catalyst consisting of 8 grams of mercuric acetate and a co-catalyst consisting of 1 gram of basic ferric acetate and 0.15 grams of cupric acetate. 0.16 moles of oxygen are absorbed during the course of the reaction. The reaction product contains 0.040 moles of unsaturated esters, 0.039 moles of C-5 glycol monoacetate and 0.0037 moles of t-amyl acetate. Olefin conversion is 0.25 moles and selectivity (defined as in example 1) is 32%.

EXAMPLE 4

130 grams of glacial acetic acid are reacted with 40 grams of 2-methyl-2-butene at 150° C. for 2 hours under oxygen pressure of 60 psig in the presence of a catalyst consisting of 8 grams of mercuric acetate and a co-catalyst consisting of 5.0 grams of basic ferric acetate and 0.75 grams of cupric acetate. 0.063 moles of oxygen are absorbed during the course of the reaction. The reaction product contains 0.055 moles of unsaturated esters, 0.014 moles of $C_5$ glycol monoacetate and 0.0111 moles of t-amyl acetate. Olefin conversion is 0.20 moles and selectivity (defined in example 1) is 42%.

EXAMPLE 5

130 grams of glacial acetic acid are reached with 20 grams of 2-methyl-2-butene at 120° C. for 7 hours under oxygen pressure of 40 psig in the presence of a catalyst consisting of 8 grams of mercuric acetate and a cocatalyst consisting of 5.0 grams of basic ferric acetate and 0.75 grams of cupric acetate. 0.053 moles of oxygen are absorbed during the course of the reaction. The reaction product contains 0.044 moles of unsaturated esters, 0.011 moles of $C_5$ glycol monoacetate and 0.005 moles of t-amyl acetate. Olefin conversion is 0.093 moles and selectivity (defined in example 1) is 63%.

EXAMPLE 6

This example compares the effectiveness of mercury and palladium as catalysts. The basic charge is as follows:

130 g. glacial acetic acid
40 g. 2-methyl-1-butene
0.15 g. $Cu(OAc)_2 \cdot 2H_2O$
1.0 g. $FeOH(OAc)_2$
10.0 g. NaOAc Two runs are made using 0.025 moles of $Hg(OAc)_2$ in one case and 0.025 moles of $PdCl_2$ in the other. In each case the temperature is 120° C. and oxygen pressure is 180 psig. The following results are obtained:

| Catalyst | Moles $O_2$ Absorbed | Time (Hours) | Moles Isoprene Precursors |
|---|---|---|---|
| $Hg(OPc)_2$ | 0.15 | 1½ | 0.11 |
| $PdCl_2$ | 0.047 | 2 | 0.019 |

The foregoing results show the better yield of isoprene precursors obtainable when the catalyst is a mercury compound as contrasted with palladium.

EXAMPLE 7

130 grams of glacial acetic acid are reacted with 40 grams of 2-methyl-2-butene at 140° C. for 3 hours under system pressure of 250 psig. The oxidizing gas is diluted air containing 10% oxygen. The catalyst consists of 8 grams of mercuric acetate and the co-catalyst consists of 0.75 grams of basic ferric acetate and 5.2 grams of cupric acetate. 0.15 moles of oxygen are absorbed during the course of the reaction. The reaction product contains by weight 11.4% esters (isoprene precursors), 72.3% acetic acid, 0.6% t-amyl acetate, and 9% unreacted olefin. Olefin selectivity (defined as in Example 1) is 72%.

EXAMPLE 8

Two runs are made as follows:
A. The reaction vessel is charged with the following materials:

150 ml. glacial acetic acid
15 ml. $H_2O$
20 g. 2 methyl-1-butene
1.0 g. basic ferric acetate
0.15 g. cupric acetate
8.0 g. mercuric acetate The vessel was pressured with $O_2$ to 100 psig at 120° C. for 2 hours.

B. The charge and reaction conditions are the same as in A except that no water is present.

Analysis of the reaction product shows that the amount of allylic ester formed is substantially identical in each run.

EXAMPLE 9

A product obtained as in Example 7 is distilled at atmospheric pressure to remove unreacted olefin, water and most of the acetic acid. The residue is then flash distilled at 10 mm. to a pot temperature of 120° C. to remove the allylic esters overhead. These esters are then pyrolyzed at 425° C. with nitrogen dilution (Vol/-Vol) over silicon carbide at a liquid hourly space velocity of about 0.5 yieldng isoprene. The yield of isoprene based on total precursors in the feed is 73%.

EXAMPLES 10-15

Several catalysts for vapor phase operation were prepared as follows:

Preparation of Catalysts for Acetoxylation Expt. Mercuric acetate-iron sulfate oil carbon A. 200 cc of coconut charcoal (6-8 mesh) are charged to a flask followed by a solution containing mercuric acetate (16g). The solution is evaporated to dryness on a rotary vacuum dryer. Ferrous sulfate (9.5g) in 100 cc of water is then charged to the mercury-coated carbon and the solution again evaporated to dryness.

Mercury-iorn-copper acetates on Alumina b. A solution of mercuric acetate (8g), ferrous acetate (2.2g) and copper acetate (1.25g) is dissolved in 200 cc of water and impregnated on 200 cc of gamma alumina (Alcoa F-1 balls 3/16' diam.).

Mercury-iron-copper and sulfuric acid in charcoal c. 16g mercuric acetate, 2.5g copper acetate, 5g acetic acid are dissolved in 150 cc of water, added to 200 cc of coconut charcoal (6-14 mole) and evaporated to drynes. When the carbon is dry, 7g of ferrous sulfate and 7.3g of sulfuric acid in 100 cc of water are added, and the mixture evaporated to dryness.

Mercury-copper-iron on Molecular Sieves

D. Norton Zeolon BP-87 1/8 11 pellets (NA Cation) are boiled 3 times in 5% acetic acid, then 3 times in distilled water. Mercuric acetate (8g), copper acetate (3.8g) and ferrous acetate (1.1g) plus 5g acetic acid in 150 cc of water are added to the treated Zeolon pellets, and the resulting mixture is boiled, and evaporated to dryness.

The following table illustrates use of these catalysts for acetoxylation of 2-methylbutene-2. For these experiments a liquid feed consisting of equal parts by weight of acetic acid and olefin is employed. The runs are made at 1 atmosphere pressure. The liquid feed is vaporized and passed over 200 cc of catalyst.

| Catalyst | Liquid Feed ($m^1$/hr) | $O_2$ (1/hr.) | Temp. ° C | Olefin Conv. % | Sel. to* Allylic Acetates % |
|---|---|---|---|---|---|
| A | 30 | 4.5 | 110° | 4.0 | 85 |
| A | 30 | 12 | 110° | 3.5 | 88 |
| A | 120 | 18 | 130° | 3.0 | 73 |
| B | 30 | 4.5 | 115° | 2.5 | 82 |
| C | 60 | 10 | 120° | 1.7 | 72 |
| D | 60 | 10 | 120° | 3.0 | 81 |

*Exclusive of t-amyl acetate which is easily reconverted to methylbutene and acetic acid.

EXAMPLE 16

17g of mercuric acetate are dissolved in water acidified with acetic acid combined with 200 cc of a commercially available carbon (Pittsburgh Coke "CAL" activated carbon) and evaporated to dryness.

The above catalyst is charged to a reactor and a feed consisting of 6.0 g/hr. of acetic acid, 18 g/hr. of methylbutene-2 and 4.0 1/hr. of oxygen are passed over the catalyst at a temperature of 125°-129° C. for 92 hours. The total allylic ester produced is 21.7g (0.17 moles). Since only 0.053 moles of mercuric acetate are employed, a catalytic oxidation is obtained.

What is claimed is:

1. A water tolerant process for the preparation of isoprene which comprises treating in the presence of a catalyst methylbutene with an aliphatic, mono-carboxylic acid having 2 to 8 carbon atoms and an oxidizing agent containing molecular oxygen at pressures of from about 0.5 atmosphere to about 70 atmospheres and at temperatures of from about 30° C. to about 200° C., the catalyst being mercury, selenium, or tellurium, an oxide, or an organic salt of said metals, or mixtures thereof, whereby to produce ester precursors which are allylic esters, and subjecting said allylic ester precursors thereby produced to pyrolysis conditions. thereby producing said isoprene.

2. A process according to claim 1 wherein the ester precursors are heated to temperatures of from about 250° C. to about 500° C. at pressures of from about 0.1 atmospheres to about 10 atmospheres, thereby producing said isoprene.

3. A process according to claim 2 wherein the ester precursors are heated to temperatures of from about 350° C. to about 450° C. at about atmospheric pressure.

4. A process according to claim 1 wherein the catalyst is used in combination with a promoter which is copper, iron, nickel, cobalt, chromium or manganese, an oxde or an organic salt of said metals, or mixtures thereof.

5. A process according to claim 4 wherein the catalyst is mercury acetate and the promoter is a combination of iron acetate and copper acetate.

6. A process according to claim 3 wherein the temperatures are about 300° C. to about 400° C.

* * * * *